US009793480B2

(12) United States Patent
Fichou et al.

(10) Patent No.: US 9,793,480 B2
(45) Date of Patent: Oct. 17, 2017

(54) METHOD FOR MANUFACTURING ORGANIC ELECTRONIC DEVICES (71) Applicant: Centre National de la Recherche Scientifique, Paris (FR)

(72) Inventors: Denis Fichou, Paris (FR); Ludovic Tortech, Gif sur Yvette (FR); Moslem Alaaeddine, Massy (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/441,640

(22) PCT Filed: Nov. 8, 2013

(86) PCT No.: PCT/IB2013/060000
§ 371 (c)(1),
(2) Date: May 8, 2015

(87) PCT Pub. No.: WO2014/072944
PCT Pub. Date: May 15, 2014

(65) Prior Publication Data
US 2015/0280125 A1   Oct. 1, 2015

(30) Foreign Application Priority Data

Nov. 8, 2012  (FR) ...................................... 12 60589

(51) Int. Cl.
*H01L 51/00* (2006.01)
*C07D 407/04* (2006.01)
(Continued)

(52) U.S. Cl.
CPC .......... *H01L 51/001* (2013.01); *C07D 407/04* (2013.01); *H01L 51/0026* (2013.01);
(Continued)

(58) Field of Classification Search
None
See application file for complete search history.

(56) References Cited

U.S. PATENT DOCUMENTS

2006/0211272 A1* 9/2006 Lee ........................ B82Y 10/00
                                                        438/789
2007/0000444 A1* 1/2007 Shimizu ................ C23C 14/044
                                                        118/720

(Continued)

FOREIGN PATENT DOCUMENTS

EP            2 488 509 A1   8/2012
WO    WO 2011/045478         4/2011

OTHER PUBLICATIONS

International Search Report and Written Opinion for Application No. PCT/IB2013/060000 dated Nov. 4, 2014.

(Continued)

*Primary Examiner* — Nathan T Leong
(74) *Attorney, Agent, or Firm* — Alston & Bird LLP (57) ABSTRACT The present invention relates to a method for manufacturing organic electronic devices including a dipyrannylidene film as an anodic interface layer, the method being carried out in a vacuum and without any exposure to air. The invention also relates to organic devices resulting from the method, more specifically to organic solar cells (OSC).

20 Claims, 3 Drawing Sheets (51) Int. Cl.
H01L 51/42 (2006.01)
H01L 51/50 (2006.01)

(52) U.S. Cl.
CPC ...... *H01L 51/0029* (2013.01); *H01L 51/0065* (2013.01); *H01L 51/42* (2013.01); *H01L 51/4253* (2013.01); *H01L 51/5088* (2013.01); *Y02E 10/549* (2013.01); *Y02P 70/521* (2015.11)

(56) References Cited

U.S. PATENT DOCUMENTS

2008/0163927 A1* 7/2008 Sohn .................. B82Y 10/00 136/263
2011/0083730 A1* 4/2011 Fichou ................ C07D 309/34 136/256

OTHER PUBLICATIONS

Guerrero, A. et al., *Oxygen Doping-Induced Photogeneration Loss in P3HT:Pcbm Solar Cells*, Solar Energy Materials & solar Cells, 100 (2012) 185-191.
Crispin et al., Journal of Polymer Science: Part B: Polymer Physics, vol. 41, (2003) 2561-2583.
Groenendaal et al., Adv. Mater. 2000, 12, No. 7.
Campbell et al., Appl. Phys. Lett., 71 (24) 3528-3530.
Kim et al., Appl. Phys. Lett., 92, (2008) 133307.
Akkerman et al., Small, 2008, 4, No. 1, 100-104.
Armstrong et al., Thin Solid Films, 445, 2003, 342-352.
Hanson et al., J. Am. Chem. Soc., vol. 127, No. 28, 2005, 127, 10058-10062.
Kahn et al., Appl. Phys. Lett., vol. 79, No. 24, 4040-4042.
Sandman et al., J. Chem. Soc., Chem. Commun., 1977, 687, 177-178.
Otsubo et al., J. Chem. Soc. Perkin Trans., 1993, 1815-1824.

* cited by examiner

AFM 2D Image

AFM 3D Images

FIGURE 3

METHOD FOR MANUFACTURING ORGANIC ELECTRONIC DEVICES

FIELD

The present invention relates to a process for the manufacture of organic electronic devices comprising a film based on dipyranylidenes of formula (I) as anode interfacial layer and to the organic devices obtained according to this process, and more particularly to the organic solar cells (OSCs) manufactured according to this process.

BACKGROUND

Current electronic systems, such as OSCs, require complex technologies which make it problematic to optimize their optical performance and electronic performance.

One of the main optimization routes consists in using, at the anode of the photovoltaic system, a conducting polymer such as poly(3,4-ethylenedioxythiophene)-poly(styrenesulfonate) (PEDOT:PSS), the latter being inserted between a tin-doped indium oxide (ITO) electrode and a photosensitive active layer (Crispin et al., Journal of Polymer Science: Part B: Polymer Physics, Vol. 41, 2561-2583 (2003)). The substrates coated with PEDOT:PSS are optically anisotropic and do not absorb very much in the visible region; the conductivity of the substrates coated with PEDOT:PSS prepared by means of commercial solutions is generally between 1 and 50 S·cm$^{-1}$.

Devices based on PEDOT:PSS today still form the subject of numerous studies (Groenendaal et al., Adv. Mater., 2000, 12, No. 7) relating to:
  the improvement in the photosensitive active layer by the use of novel absorbent materials, by the charge network structuring or also by the improvement in the transportation of the charges, and
  the improvement in the interfaces by virtue of a better quality of the contacts or a collecting of the charges.

Thus, the anode interfacial layers used in electronic devices should exhibit:
  good electronic properties and more particularly a high conductivity, and also a suitable work function which makes it possible to optimize the energy barrier at the interface between the ITO electrode and the photosensitive active layer, facilitating the collection of the positives charges,
  good optical properties which are characterized by a minimum absorption, and
  good stability and an ease of forming which makes possible the formation of homogeneous and continuous films.

Work function is understood to mean the minimum energy, measured in electron volts (eV), necessary in order to extract an electron from the Fermi level of a metal to a point located at infinity outside the metal. The photoelectric effect consists of release of an electron when a photon having an energy greater than the work function arrives on the metal. The difference between the energy of the incident photon and the work function is supplied to the electron in the form of kinetic energy. Thus, the photoelectric work function is calculated according to the formula:

$$\varphi = h \cdot f_0$$

where h is Planck's constant and $f_0$ is the minimum frequency of a photon starting from which photoelectric emission occurs.

The work function of the electrodes plays a crucial role in the field of plastic electronics because it influences the distribution of the internal electric field and the height of the energy barrier between the electrode and the photosensitive active layer of the device. This barrier greatly influences the injection of the charge carriers, in particular in the case of organic light-emitting diodes (OLEDs), or, on the contrary, dominates the collection of the charges of the active layer towards the electrode, such as, for example, in the case of OSCs. In order to facilitate the transportation of the holes, materials exhibiting high work functions are preferred as anode.

Currently, the most commonly used devices are devices based on PEDOT:PSS. However, when it is used as interfacial layer on ITO electrodes, PEDOT:PSS has to be applied in the form of a thin film having a thickness of less than approximately one hundred nanometers, in order to guarantee a high optical transmission; the PEDOT:PSS film exhibits, in this case, a low conductivity. Surface defects and holes can also appear at the surface of the PEDOT:PSS film when the polymer layers applied are excessively thin. On the other hand, when it is applied as a thicker layer (between 150 and 200 nm in thickness), i.e. in order to achieve higher conductivities which make possible lateral transport of the photocurrent, a loss at the level of the optical transmission coefficient is then observed.

Systems based on PEDOT:PSS also have other disadvantages:
  the interface between the PEDOT:PSS films and the ITO-based electrodes is unstable, the indium atoms diffusing into the polymer layer and detrimentally affecting its performance,
  the electric contact between the PEDOT:PSS films and the ITO-based electrodes is slight, the polymer layer not accessing numerous electronically active sites of the surface of the ITO electrode, which increases the series resistances and greatly decreases the collection of holes at the electrode,
  the conductivity and the roughness of the PEDOT:PSS layers are dependent on the application conditions and in particular on the moisture content and on the annealing temperatures.

Replacement routes for the use of conducting polymers at the anode interface have also been envisaged, such as, for example:
  the use of monolayers (Campbell et al., Appl. Phys. Lett., 71 (24), 3528-3530; Kim et al., Appl. Phys. Lett., 92, 133307 (2008); Akkerman et al., Small, 2008, 4, No. 1, 100-104; Armstrong et al., Thin Solid Films, 445, 2003, 342-352), the latter generally being covalently bonded, by the chemical or electrochemical route, to the surface of the ITO electrode. However, these monolayers are not very thick (a few tens of angstroms) and result in unequal covering of the substrates which they functionalize, allowing roughnesses to remain and thus resulting in interfaces of mediocre quality,
  the use of charge transfer complexes (Hanson et al., J. Am. Chem. Soc., Vol. 127, No. 28, 2005, 127, 10058-10062; Kahn et al., Appl. Phys. Lett., Vol. 79, No. 24, 4040-4042), the latter nevertheless exhibiting the disadvantage of having energy levels which are difficult to adjust.

SUMMARY

The inventors have demonstrated, in the application WO 2011/045478, the properties of substrates coated with dipyranylidene-based films used as anode interfacial layer in electronic devices.

They have now discovered that a process for the manufacture of organic electronic devices employing such dipyranylidene compounds, carried out under vacuum and in the absence of any exposure to the air, makes it possible to significantly improve the performance of the organic devices resulting from such a process.

Such a process avoids any gradual degradation of the organic electronic devices manufactured and considerably improves their photocurrent densities and their conversion efficiencies. Conversion efficiencies of greater than 3% and which can range up to 6% were obtained for photovoltaic cells manufactured according to the process of the invention, these results being to be compared with the maximum values of 1.5% obtained for the devices described in the application WO 2011/045478.

The first subject matter of the present invention is thus a process for the manufacture of an organic electronic device carried out in the absence of any exposure to the air and comprising at least the following stages:

(i) the deposition by vacuum evaporation, preferably in an ultrahigh vacuum chamber, on a substrate, of a film comprising at least one compound of following formula (I):

in which:

Xa and Xb, which are identical or different, are chosen from N, P, O, S, Se or Te atoms, $R_1$, $R_2$, $R_3$ and $R_4$, which are identical or different, represent a group chosen from aryl or heteroaryl rings having from 4 to 10 carbon atoms, it being possible for said aryl or heteroaryl rings optionally to be substituted by one or more halogen atoms or —OH, —CN, —NO$_2$ groups, alkyl having from 1 to 30 carbon atoms, alkoxy —OC$_n$H$_{2n+1}$ or ester —C(O)OC$_n$H$_{2n+1}$ groups, in which $0 \leq n \leq 16$, (ii) the deposition under an inert atmosphere of a photosensitive active layer, (iii) optionally, the annealing under an inert atmosphere of the photosensitive active layer deposited during stage (ii), (iv) the deposition under an inert atmosphere of an active layer for the dissociation of the excitons, said layer preferably being based on lithium fluoride (LiF), (v) the deposition under an inert atmosphere of a layer acting as cathode electrode.

All the stages of the process are carried out under vacuum or under an inert atmosphere, in order for the organic electronic device never to be exposed to the air during its manufacture. When the stages are carried out under an inert atmosphere, they are preferably carried out under an inert atmosphere of nitrogen or argon.

In addition, the inventors have found that the film comprising a compound of formula (I) in combination with a conducting intermediate layer can also, by itself alone, act as conducting electrode, without it being necessary to apply it to a conducting substrate, such as ITO. This improvement makes it possible in particular to manufacture ITO-free devices.

Within the meaning of the present invention:

alkoxy is understood to mean an O-alkyl group in which the alkyl group is a saturated, linear or branched, aliphatic hydrocarbon group;

halogen atom is understood to mean a bromine, chlorine, iodine or fluorine atom, the designations bromine, chlorine and fluorine being preferred;

aryl group denotes any functional or substituent group derived from at least one aromatic ring; an aromatic ring corresponds to any flat mono- or polycyclic group comprising a delocalized π system in which each atom of the ring comprises a p orbital, said p orbitals overlapping one another;

heteroaryl group denotes any functional or substituent group derived from at least one aromatic ring as defined above and comprising at least one heteroatom chosen from N, P, O and S.

The compound of formula (I) of the invention is preferably present in the film in the form of particles having a mean diameter of less than or equal to 300 nm, preferably of less than or equal to 250 nm, and more preferably still of less than or equal to 200 nm.

According to an advantageous embodiment, the Xa and Xb atoms of the compound of formula (I) are identical and are chosen from O, S or Se atoms, and preferably Xa=Xb=O.

The aryl or heteroaryl rings $R_1$, $R_2$, $R_3$ and $R_4$ of the compound of formula (I) are for their part preferably chosen from phenyl, naphthyl, anthracyl, benzoxazolyl, thiophenyl or alkoxythiophenyl, furyl, pyrrolyl, pyridyl, pyrazyl, pyrazolyl, pyridazyl, pyrimidyl, triazyl, imidazolyl, oxazolyl, indyl, indazolyl, quinolyl and quinoxalyl rings, and more preferably $R_1$, $R_2$, $R_3$ and $R_4$ are identical and represent a phenyl.

In addition to the compound of formula (I), the film of stage (i) can also comprise other constituents and more particularly electron-accepting molecules which result in the formation of charge transfer complexes, such as 7,7,8,8-tetracyano-p-quinodimethane (TCNQ) or tetrafluoro-7,7,8,8-tetracyano-p-quinodimethane (F$_4$TCNQ). These electron-accepting molecules are introduced in a low amount with respect to the compound of formula (I). Preferably, the electron-accepting molecules/compounds of formula (I) ratio by weight is between 1/99 and 5/95. They act as doping agents by enhancing the intrinsic properties of conduction of the holes of the compound of formula (I).

According to an advantageous embodiment, the film comprising at least one compound of formula (I) deposited during stage (i) has a thickness of less than 45 nm, preferably of less than or equal to 30 nm, and more preferably still of less than or equal to 15 nm.

The deposition by vacuum evaporation of stage (i) makes it possible to sublime the compound of formula (I). It can be carried out by chemical vapor deposition CVD, this technique consisting in adding a metal precursor to a liquid carbon source (such as toluene, benzene or cyclohexane), the solution then being converted into fine droplets transported by an inert gas as far as an oven. In practice, the compound of formula (I) is placed, in the powder form, in a crucible, then covered with alumina and subsequently heated under vacuum until the compound of formula (I) changes from a solid state to the liquid state (sublimation). The vapor stream of the compound of formula (I) is then directed towards the substrate so as to cover it with a film composed of the compound of formula (I). Stage (i) is carried out at a rate of evaporation of less than 1 Å/s, preferably of less than or equal to 0.4 Å/s, and more preferably still of less than or equal to 0.1 Å/s.

The substrate of stage (i) can be an insulating or conducting substrate. This substrate can be rigid or flexible. In the case of an insulating substrate, it is preferably chosen from glass or polymers, such as polyethylene terephthalate (PET), amorphous polyethylene (amorphous PE) and amorphous polystyrene (amorphous PS). In the case of a conducting substrate, it is preferably chosen from metal oxides, such as aluminum oxide, indium oxide, tin oxide, iridium oxide, silicon oxide, iron oxide and copper oxide and more preferably still tin-doped indium oxide (ITO). When the substrate is a conducting substrate, it may have been deposited beforehand on a base support, preferably made of glass or based on polymer, said deposition being carried out in an ultrahigh vacuum chamber.

Advantageously, the distance between the source of the compound of formula (I) and the substrate during stage (i) is between 10 and 40 cm, and preferably between 25 and 35 cm.

The process of the invention can comprise, between stages (i) and (ii), the deposition of a conducting intermediate layer, said layer preferably being a PEDOT:PSS layer. This stage is carried out in a glove box under an inert atmosphere. Preferably, the deposition of the conducting intermediate layer is carried out by spin coating.

According to an advantageous embodiment, the deposition of a photosensitive active layer during stage (ii) is carried out in a glove box placed under an inert atmosphere of nitrogen or argon. Said deposition is preferably carried out by spin coating.

Preferably, the photosensitive active layer of stage (ii) is a layer composed of at least two materials which absorb strongly in the visible region, one being an electron donor and the other being an electron acceptor, this layer undergoing ultrarapid charge transfer and creating positive charges (holes) and negative charges (electrons) under the effect of light irradiation. This photosensitive active layer can be the combination of phthalocyanine, pentacene, thiophene, triphenylamine or p-type polymer derivatives with molecules such as fullerene derivatives or perylenes, the P3HT:PCBM mixture being the preferred combination.

The photosensitive active layer deposited during stage (ii) can also be coated with an active layer for the dissociation of the excitons (or EBL for Exciton Blocking Layer), which can be based on lithium fluoride (LiF) in the OSC devices or based on alumina in the OLED or PLED devices. Advantageously, the active layer for dissociation of the excitons exhibits a thickness of less than 10 Å, preferably of less than 8 Å, and more preferably still of between 5 and 7 Å.

The optional stage (iii) of annealing under an inert atmosphere is advantageously carried out in a tubular oven, at a temperature of between 30 and 150° C., preferably between 80 and 150° C. and more preferably still of approximately 120° C., for a period of time of between 1 minute and 24 hours, preferably between 5 and 20 minutes, and more preferably still for approximately 10 minutes.

Stage (iv) of deposition under an inert atmosphere of an active layer for the dissociation of the excitons can be a deposition by the dry route carried out under an inert atmosphere, for example by chemical vapor deposition CVD, this deposition preferably being carried out at a rate of evaporation of less than 1 Å/s, more preferably of less than or equal to 0.4 Å/s, and more preferably still of less than or equal to 0.1 Å/s. The deposition by the dry route of stage (iv) can be carried out at an annealing temperature of between 80 and 120° C. and under a pressure of between $10^{-4}$ and $10^{-8}$ mbar, for a period of time of between 2 and 4 hours.

According to a preferred embodiment, the deposition of stage (v) is carried out in an ultrahigh vacuum chamber. This stage (v) can be carried out by the dry route at a rate of evaporation of less than or equal to 3 Å/s, and preferably between 0.1 and 2 Å/s.

Advantageously, the layer of stage (v) acting as cathode electrode is based on aluminum, gold, calcium, copper, samarium, platinum, palladium, chromium, cobalt or iridium.

According to a particularly preferred embodiment, in the device manufactured according to the process of the invention, the substrate is made of glass or plastic or is based on ITO, and the photosensitive active layer is based on P3HT:PCBM.

Another subject matter of the invention is an organic electronic device obtained according to the process of the invention, said device being chosen from organic light-emitting diodes (OLEDs), polymer light-emitting diodes (PLEDs), organic field-effect transistors (OFETs) and organic solar cells (OSCs).

The invention very particularly relates to an organic solar cell (OSC) obtained according to the process of the invention, in which the substrate is based on polymer or an oxide and, in the latter case, is preferably based on ITO.

The compounds of formula (I) can be synthesized according to methods known to a person skilled in the art, such as those described by Sandman et al., J. Chem. Soc., Chem. Commun., 1977, 687, 177-178, and Otsubo et al., J. Chem. Soc. Perkin Trans., 1993, 1815-1824.

BRIEF DESCRIPTION OF THE DRAWINGS

In addition to the preceding provisions, the invention also comprises other provisions which will emerge from the description which will follow, which refers to examples of the implementation of the process of the invention and to the evaluation of OSC devices manufactured according to this process, and also to the appended drawings, in which.

DETAILED DESCRIPTION

EXPERIMENTAL PART

A substrate coated with a film comprising 4,4'-bis(2,6-diphenylpyranylidene) (DIPO-Φ$_4$) as compound of formula (I) was prepared according to the procedure described below.

The formula of DIPO-Φ$_4$ is as follows:

A—Synthesis of DIPO-Φ$_4$

Stage 1: Synthesis of 1,5-diphenyl-1,5-pentadione

A solution of glutaryl chloride (10 mmol, 1.3 ml) dissolved in anhydrous dichloromethane (20 ml) is introduced under an inert atmosphere into a 100 ml two-necked round-bottomed flask. Aluminum chloride (30 mmol, 4.00 g) is added to the mixture, which immediately turns orange-yellow in color. A solution of benzene (20 mmol, 1.8 ml) dissolved in anhydrous dichloromethane (10 ml) is added dropwise at ambient temperature. The solution becomes intense red. The mixture is subsequently brought to reflux for 24 hours and turns brown-black in color. The mixture is subsequently brought back to ambient temperature and then run, with stirring, into a crystallizing dish containing 20 ml of water acidified to 10%. A black solid is formed and is then filtered off on a Buchner funnel. The organic phase, which is yellow in color, is subsequently extracted with ethyl acetate, dried over MgSO$_4$, filtered, concentrated on a rotary evaporator and recrystallized from 20 ml of methanol. The product obtained is a white solid having a weight of 680 mg. The reaction yield is 27%.

TLC (eluent: petroleum ether/ethyl acetate 1:1): 0.75

$^1$H NMR (CDCl$_3$, 400 MHz): δ=7.98 (d, 4H, $^3$J=7.1 Hz), 7.57 (t, 2H, $^3$J=7.3 Hz), 7.47 (t, 4H, $^3$J=7.3 Hz), 3.13 (t, 4H, $^3$J=6.9 Hz), 2.21 (quint., 2H, $^3$J=6.9 Hz)

Stage 2: Synthesis of 2,6-diphenylpyrylium perchlorate

The 1,5-diphenyl-1,5-pentadione prepared during stage 1 (10 mmol, 2.52 g) is mixed, in a 100 ml two-necked round-bottomed flask, with phosphorus pentasulfide (15 mmol, 3.34 g), acetic acid (60 ml) and FeCl$_3$ (60 mmol, 6.40 g) and then brought to reflux for 3 hours. The solution then becomes orange and a white precipitate is formed. The precipitate is removed by filtration through a sintered glass funnel and then washed with hot acetic acid. The solution is concentrated on a rotary evaporator and recrystallized by addition of ether (500 ml). The precipitate obtained is filtered off on a sintered glass funnel and then dried in a rotary evaporator. The product obtained is a red solid having a weight of 850 mg. The reaction yield is 24%.

$^1$H NMR (CD$_3$CN, 400 MHz): δ=8.90 (t, 1H), 8.52 (d, 2H), 8.18 (d, 4H), 7.60 (t, 4H), 7.50 (t, 2H).

Stage 3: Synthesis of 4,4'-bis(2,6-diphenylpyranylidene) (DIPO-Φ$_4$)

The solution of 2,6-diphenylpyrylium perchlorate (10 mmol, 3.50 g) is dissolved in 200 ml of distilled acetonitrile in a 250 ml two-necked round-bottomed flask and then the mixture is brought to reflux under an inert atmosphere for 2 hours. Zinc powder (30 mmol, 1.96 g) is added in small fractions and the mixture is brought to reflux for 24 hours. The solution is filtered, rinsed with toluene and evaporated on a rotary evaporator. A black oil is obtained which is recrystallized from a hexane/ethanol 1:1 mixture. After purification by TLC (eluent: petroleum ether/ethyl acetate 8:2), a black solid weighing 650 mg is obtained. The reaction yield is 13%.

IR (cm$^{-1}$): 2920, 1650, 1605, 1550, 1488, 1441, 1229, 1071, 750, 685.

B—Manufacture of an Organic Solar Cell (OSC) According to the Process of the Invention The preparation of the OSC devices of the invention takes place in several:

A 1st stage which has the objective of preparing an ITO substrate with a width of 10 mm and a length of 25 mm, to avoid any short-circuit phenomenon. An ITO electrode on a glass support is immersed with an FeCl$_3$+HCl solution heated at 50° C. for 2 minutes, successively rinsed in different solvent baths: ethyl acetate, Decon (5% aqueous solution), ethanol and acetone, and then stripped in a UV/ozone chamber by forced oxidation.

A 2nd stage of deposition of 4,4'-bis(2,6-diphenylpyranylidene) (DIPO-Φ$_4$) on a glass/ITO substrate by vacuum evaporation (pressure=10$^{-7}$ mbar; rate of deposition=0.1 Å/s), to form a layer with a thickness of 10 nm. The distance between the crucible (crucible made of molybdenum covered with alumina) containing DIPO-Φ$_4$ and the glass/ITO substrate is 35 cm. The crucible is heated by the Joule effect (0.5 V, 50 A, 25 W). The thickness of the layer is monitored using a quartz balance calibrated for aluminum tris(8-hydroxyquinolinate) (Alq3) (vibrational frequency=6.01 MHz, ±1%). The Alq3 molecule is used as reference standard for the deposition of all the organic molecules. The frequency of the quartz crystal of 6.01 MHz is the nominal working frequency.

A 3rd stage during which the glass/ITO/DIPO-Φ$_4$ substrate is brought back to atmospheric pressure under an inert nitrogen atmosphere and then transferred into a glove box via an airlock. A conducting intermediate layer of PEDOT:PSS (concentrated suspension at a level of 0.29% by weight in aqueous phase, Sigma-Aldrich) is deposited by spin coating at a rate of 2000 revolutions/min for 50 seconds.

A 4th stage during which the glass/ITO/DIPO-Φ$_4$/PEDOT:PSS substrate is covered with a deposit of a photosensitive active layer of P3HT:PCBM at the following concentrations: 15 mg P3HT and 12 mg PCBM (in 1 ml of chlorobenzene), at 1000 revolutions/min for 20 seconds, 1200 revolutions/min for 20 seconds and finally 2000 revolutions/min for 10 seconds. The thicknesses obtained by this method are of the order of 120±10 nm.

A 5th stage during which the glass/ITO/DIPO-Φ$_4$/PEDOT:PSS/P3HT:PCBM device is subsequently transferred into a UHV (Ultra High Vacuum) chamber where deposition of lithium fluoride LiF (Sigma-Aldrich) by thermal evaporation under stable evaporation conditions of 0.01 Å/s, until a layer having a thickness of 0.5 nm is obtained, and then deposition of aluminum by thermal evaporation under stable evaporation conditions of 0.4 Å/s and under a pressure of 10$^{-7}$ mbar, until an aluminum layer with a thickness of 80 nm is obtained, are successively carried out.

A 6th stage during which the glass/ITO/DIPO-Φ$_4$/PEDOT:PSS/P3HT:PCBM/LiF/Al device is subsequently transferred into a glove box placed at atmospheric pressure and under an inert nitrogen atmosphere via an airlock.

Finally, deposition of silver lacquer (area ~1×1 mm$^2$) is carried out using a fine object (needle tip) on the aluminum layer in order to make possible good electrical contact of the aluminum electrode. Once deposited, the lacquer is dried at ambient temperature for 45 minutes.

C—Characterization of the OSC Device of the Invention

The current/voltage characteristic of the devices in darkness and under illumination are measured under an inert nitrogen atmosphere using a device for the physical measurement of currents (Keithley 2406) and a microtip station.

The characteristics in darkness are determined by placing a black veil over the devices in order to prevent diffused light from having influence.

The current/voltage characteristics of the devices under illumination are measured on an optical bench equipped:

1) with a xenon lamp (Oriel, 150 W) which simulates the spectrum of the sun and delivers a power of 75 or 100 mW·cm$^{-2}$ at the OSC devices,
2) with a monochromator (Cornerstone CS120),
3) with an IR filter placed between the lamp and the OSC devices in order to prevent the latter from overheating,
4) with synchronous detection (of HDTS brand), and
5) with an optical chopper (of Lot Oriel brand).

The solar simulator is calibrated so as to release the solar nominal power such as has been set by international conventions for this type of device (75 or 100 mW/cm$^2$). The measurements can be carried out under white light or under monochromatic light. Under white light, the component is contacted using the microtip station and is exposed to light using the solar simulator. The electrical measurement device (Keithley 2406) records under zero or variable field the current extracted from the OSC device of the invention. This measurement makes it possible to determine the external conversion efficiency PCE (Power Conversion Efficiency) of the device.

The current/voltage characteristics in darkness and under illumination by white light make it possible to evaluate the performance and the behavior of the OSC devices of the invention. The following parameters can thus be defined:
the short-circuit current Isc obtained for a zero voltage, this current being proportional to the incident illumination (Jsc=Isc/S, where S is the area of the device),
the open-circuit voltage Voc measured for a zero current,
Imax and Vmax are the IN coordinates (Pmax=Imax× Vmax),
the Form Factor (FF), equal to: FF=(Vmax×Imax)/(Voc× Isc)

Figure 1:
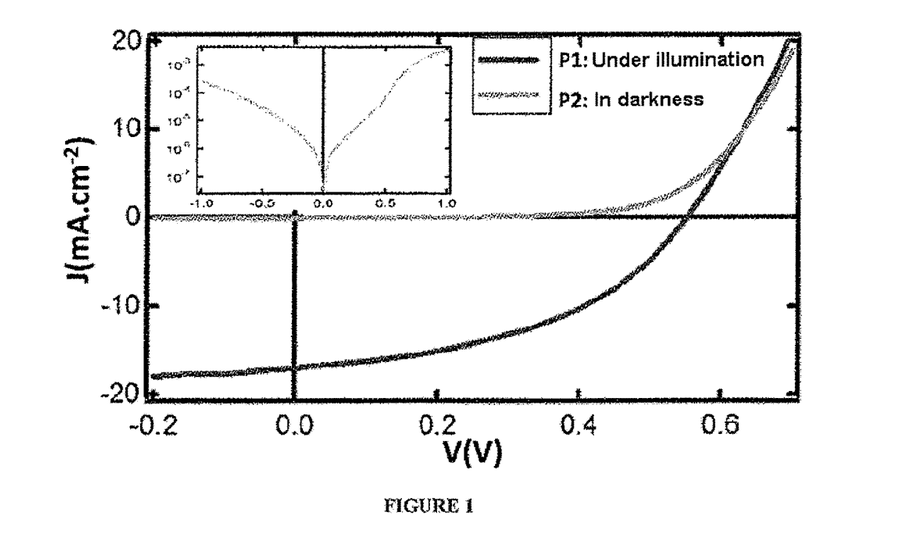
FIG. 1 represents the current/voltage curves of an OSC device according to the invention (light curve: in darkness; dark curve: under AM1.5G illumination (75 mW·cm$^{-2}$))

The current/voltage curves obtained for the OSC device of the invention are represented in FIG. 1 and the corresponding main photovoltaic characteristics are collated in the following Table I:

TABLE I

| Vmax (mV) | Imax (µA) | Isc (µA) | Voc (mV) | Photogenerated current Jsc (mA · cm$^{-2}$) | FF (%) | PCE (%) |
|---|---|---|---|---|---|---|
| 366 | 0.516 | 0.766 | 550 | 17.1 | 45 | 6.0 |

It is found that the OSC device of the invention exhibits a better performance than those obtained with the devices described in the application WO 2011/045478 and in particular:
the open-circuit voltages Voc are superior,
the short-circuit currents Isc and the photocurrent densities Jsc are superior.

Consequently, the external conversion efficiency (PCE=6.0% instead of 1.5%) is much greater than that of the devices described in application WO 2011/045478.

Figure 2:
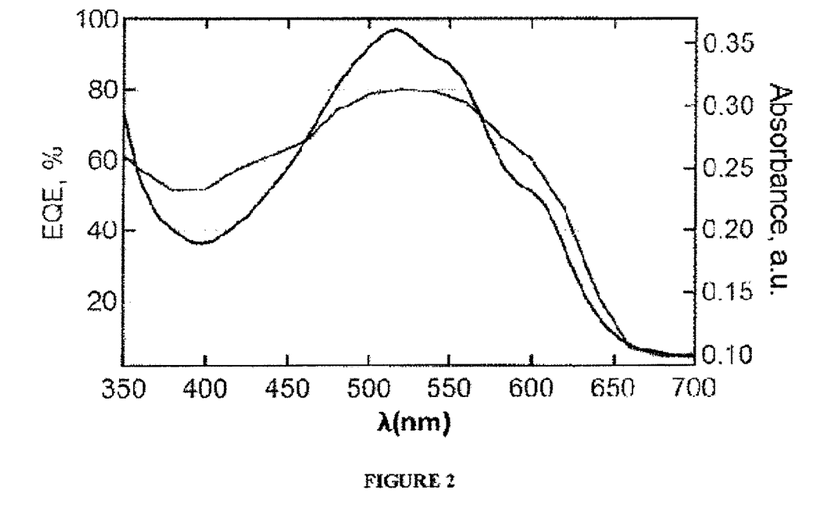
FIG. 2 represents the EQE spectrum of the device of the invention (curve exhibiting a maximum at 80% for a wavelength of approximately 530 nm) and the absorption spectrum of the ITO/DIPO-Φ$_4$/PEDOT:PSS/P3HT:PCBM device.

Under monochromatic illumination, the light of the lamp passes through a monochromator (Cornerstone CS120) and a pulse chopper to release a pulsed monochromatic light. The electrical measurement is then carried out using synchronous detection. This type of measurement makes it possible to characterize the action spectrum and the external quantum efficiency (EQE) of the photovoltaic device. FIG. 2 presents the EQE characteristics of the OSC device of the invention. It is found that the EQE spectrum follows the absorption spectrum of the P3HT:PCBM active material with a very high maximum at 80% for a wavelength of approximately 530 nm.

Figure 3:
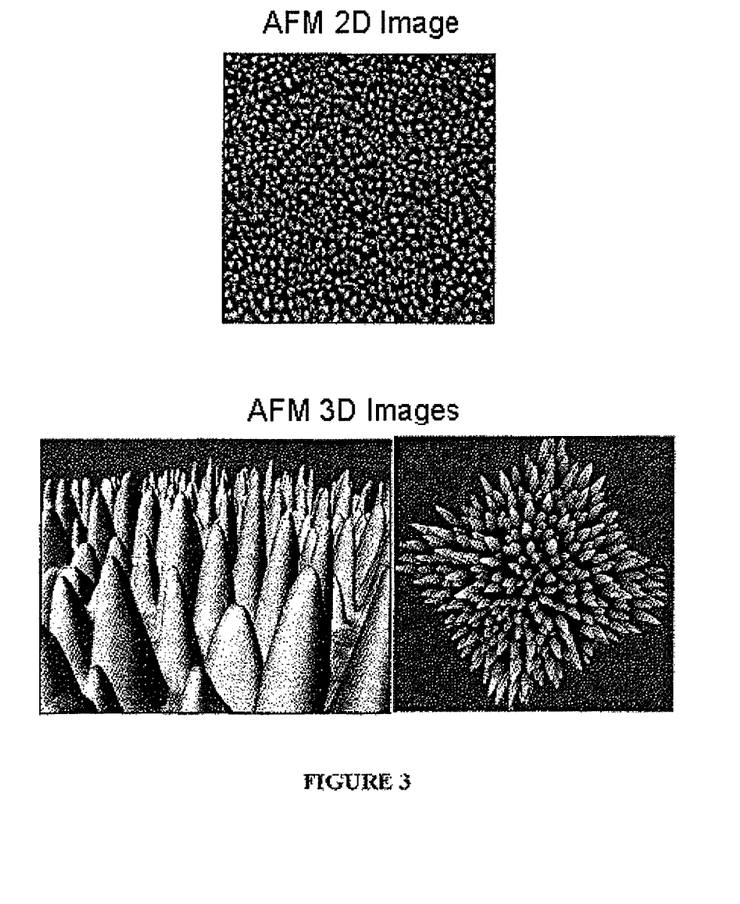
FIG. 3 shows AFM (2D and 3D) microscopy images of the anode layer of an OSC device according to the invention.

Finally, FIG. 3 shows AFM (2D and 3D) microscopy images which reveal a needle-shaped nanostructuring of the anode layer of the OSC device of the invention.

The invention claimed is:

1. A process for the manufacture of an organic electronic device, comprising at least the following stages:
(i) the deposition by vacuum evaporation, on a substrate, of a film comprising at least one compound of following formula (I):

in which:
Xa and Xb, which are identical or different, are chosen from N, P, O, S, Se or Te atoms,
$R_1$, $R_2$, $R_3$ and $R_4$, which are identical or different, represent a group chosen from aryl or heteroaryl rings having from 4 to 10 carbon atoms, said aryl or heteroaryl rings being optionally substituted by one or more halogen atoms or —OH, —CN, —NO$_2$ groups, alkyl having from 1 to 30 carbon atoms, alkoxy —OC$_n$H$_{2n+1}$ or ester —C(O)OC$_n$H$_{2n+1}$ groups, in which 0≤n≤16,
(ii) the deposition under an inert atmosphere of a photosensitive active layer,
(iii) optionally, the annealing under an inert atmosphere of the photosensitive active layer deposited during stage (ii),
(iv) the deposition under an inert atmosphere of an active layer for the dissociation of the excitons,
(v) the deposition under an inert atmosphere of a layer acting as cathode electrode,
said process being carried out with the exclusion of air, and wherein the organic electronic device has a power conversion efficiency greater than or equal to 3%.

2. The process as claimed in claim 1, in which the Xa and Xb atoms of the compound of formula (I) are identical and are chosen from O, S or Se atoms.

3. The process as claimed in claim 1, in which the aryl or heteroaryl rings $R_1$, $R_2$, $R_3$ and $R_4$ of the compound of formula (I) are chosen from phenyl, naphthyl, anthracyl, benzoxazolyl, thiophenyl or alkoxythiophenyl, furyl, pyrrolyl, pyridyl, pyrazyl, pyrazolyl, pyridazyl, pyrimidyl, triazyl, imidazolyl, oxazolyl, indyl, indazolyl, quinolyl and quinoxalyl rings.

4. The process as claimed in claim 1, in which the deposition by vacuum evaporation of stage (i) is carried out in an ultrahigh vacuum chamber.

5. The process as claimed in claim 1, in which the deposition by vacuum evaporation of stage (i) is carried out at a rate of evaporation of less than 1 Å/s.

6. The process as claimed in claim 1, in which the film comprising at least one compound of formula (I) has a thickness of less than 45 nm.

7. The process as claimed in claim 1, in which the substrate is chosen from insulating substrates or conducting substrates.

8. The process as claimed in claim 1, in which the distance between the source of the compound of formula (I) and the substrate is between 10 and 40 cm, during stage (i).

9. The process as claimed in claim 1, in which a stage of deposition of a conducting intermediate layer, is carried out between stages (i) and (ii).

10. The process as claimed in claim 1, in which the deposition of stage (ii) is carried out in a glove box placed under an inert atmosphere of nitrogen or argon.

11. The process as claimed in claim 1, in which the deposition of stage (ii) is carried out by spin coating.

12. The process as claimed in claim 1, in which the annealing of stage (iii) is carried out in a tubular oven, at a temperature of between 30 and 150° C., for a period of time of between 1 minute and 24 hours.

13. The process as claimed in claim 1, in which the deposition of stage (iv) is carried out by the dry route, at a rate of evaporation of less than 1 Å/s.

14. The process as claimed in claim 13, in which the deposition by the dry route is carried out at an annealing temperature of between 80 and 120° C. and under a pressure of between $10^{-4}$ and $10^{-8}$ mbar, for a period of time of between 2 and 4 hours.

15. The process as claimed in claim 1, in which the deposition of stage (v) is carried out in an ultrahigh vacuum chamber.

16. The process as claimed in claim 1, in which the deposition of stage (v) is carried out by the dry route at a rate of evaporation of less than or equal to 3 Å/s.

17. The process as claimed in claim 1, in which the layer acting as cathode electrode deposited during stage (v) is based on aluminum, gold, calcium, copper, samarium, platinum, palladium, chromium, cobalt or iridium.

18. The process as claimed in claim 1, in which the substrate is made of glass or plastic or is based on tin-doped indium oxide (ITO), and the photosensitive active layer is P3HT:PCBM.

19. The process as claimed in claim 1, wherein said active layer for the dissociation of the excitons is based on lithium fluoride (LiF).

20. The process as claimed in claim 1, wherein the organic electronic device has a power conversion efficiency from 3 to 6%.

* * * * *